United States Patent
Kuwabara

(10) Patent No.: US 8,981,291 B2
(45) Date of Patent: Mar. 17, 2015

(54) METHOD FOR MEASURING FILM THICKNESS OF SOI LAYER OF SOI WAFER

(75) Inventor: Susumu Kuwabara, Annaka (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 0 days.

(21) Appl. No.: 14/009,182

(22) PCT Filed: Apr. 11, 2012

(86) PCT No.: PCT/JP2012/002503
§ 371 (c)(1),
(2), (4) Date: Oct. 1, 2013

(87) PCT Pub. No.: WO2012/153462
PCT Pub. Date: Nov. 15, 2012

(65) Prior Publication Data
US 2014/0027633 A1 Jan. 30, 2014

(30) Foreign Application Priority Data
May 10, 2011 (JP) ................. 2011-105565

(51) Int. Cl.
*H01J 37/26* (2006.01)
*G01B 15/02* (2006.01)
*G01N 23/225* (2006.01)
(Continued)

(52) U.S. Cl.
CPC .............. *G01B 15/02* (2013.01); *G01B 15/025* (2013.01); *G01N 23/2252* (2013.01); *H01L 22/12* (2013.01); *G01N 2223/6116* (2013.01); *H01L 21/7624* (2013.01)
USPC ........... 250/307; 250/305; 250/310; 250/311; 250/492.3

(58) Field of Classification Search
USPC ................. 250/305, 306, 307, 309, 310, 311, 250/492.1, 492.3
See application file for complete search history.

(56) References Cited

U.S. PATENT DOCUMENTS 6,248,603 B1  6/2001  Jones et al.
6,787,773 B1  9/2004  Lee
(Continued)

FOREIGN PATENT DOCUMENTS

JP  B-49-39699  10/1974
JP  A-2-266208  10/1990
(Continued)

OTHER PUBLICATIONS

International Search Report issued in International Patent Application No. PCT/JP2012/002503 dated May 15, 2012.
(Continued)

*Primary Examiner* — Nicole Ippolito
(74) *Attorney, Agent, or Firm* — Oliff PLC

(57) ABSTRACT

A method for measuring a film thickness of an SOI layer of an SOI wafer including at least an insulator layer and the SOI layer which is formed on the insulator layer and is formed of a silicon single crystal, wherein a surface of the SOI layer is irradiated with an electron beam, characteristic X-rays are detected from a side of the SOI layer surface irradiated with the electron beam, the characteristic X-rays being generated by exciting a specific element in the insulator layer with the electron beam that has passed through the SOI layer and has been attenuated in the SOI layer, and the film thickness of the SOI layer is calculated on the basis of an intensity of the detected characteristic X-rays.

5 Claims, 1 Drawing Sheet

(51) Int. Cl.
  *H01L 21/66* (2006.01)
  *H01L 21/762* (2006.01)

(56) References Cited

U.S. PATENT DOCUMENTS

| | | | |
|---|---|---|---|
| 6,924,484 B1 | 8/2005 | Wang et al. | |
| 7,046,019 B1 | 5/2006 | Sarfaty et al. | |
| 7,220,964 B1 | 5/2007 | Gao et al. | |
| 2004/0130718 A1 | 7/2004 | Krishnan | |
| 2008/0029822 A1* | 2/2008 | Tsuchiya et al. | 257/369 |

FOREIGN PATENT DOCUMENTS

| | | |
|---|---|---|
| JP | A-5-45147 | 2/1993 |
| JP | A-10-221047 | 8/1998 |
| JP | A-2002-213935 | 7/2002 |
| JP | A-2003-536084 | 12/2003 |
| JP | A-2004-335695 | 11/2004 |
| JP | A-2006-524828 | 11/2006 |
| JP | A-2009-016766 | 1/2009 |
| WO | WO 01/95365 A1 | 12/2001 |
| WO | WO 2004/076969 A1 | 9/2004 |

OTHER PUBLICATIONS

Office Action issued in Japanese Patent Application No. 2011-105565 dated Oct. 29, 2013 (with partial translation).
International Preliminary Report on Patentability issued in International Application No. PCT/JP2012/002503 dated Nov. 21, 2013.
Office Action issued in Japanese Application No. 2011-105565 dated Aug. 5, 2014 (with partial translation).
Oct. 17, 2014 Search Report issued in European Application No. 12782573.5.
Pascual R., "Thin Film Thickness Measurement Using the Energy-Dispersive Spectroscopy Technique in a Scanning Electron Microscope," Thin Solid Films, vol. 185, pp. 279-286, 1990.

* cited by examiner

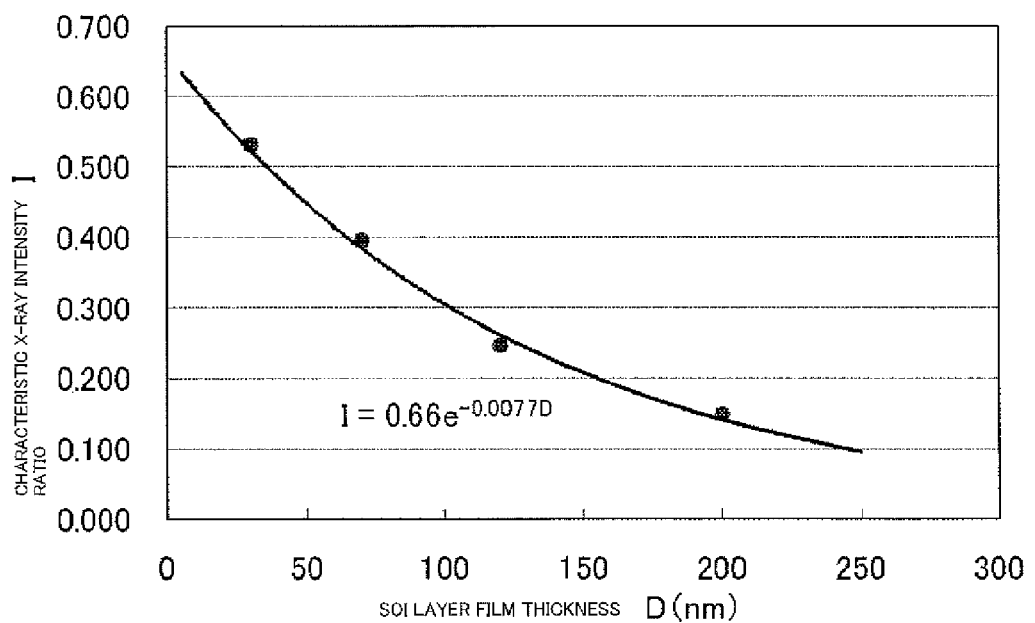

METHOD FOR MEASURING FILM THICKNESS OF SOI LAYER OF SOI WAFER

TECHNICAL FIELD

The present invention relates to a method for measuring a film thickness of an SOI layer of an SOI wafer, the method that measures the film thickness of the SOI layer of the SOI wafer with high spatial resolution, the SOI wafer used for fabrication of a semiconductor device.

BACKGROUND ART

In recent years, as design rules have become finer, the film thickness distribution of SOI layer of an SOI wafer used for fabrication of an SOI device, in particular, fabrication of an FD-SOI (Fully Depleted SOI) device has had an influence on a device fabrication process and, consequently, the transistor characteristics. In an integrated circuit, it is important to make the characteristics of the transistors forming the circuit uniform.

Therefore, in an FD-SOI device, it is important to measure the film thickness of an SOI layer of an SOI wafer accurately. While the devices have become finer and transistors having a size of several dozen nanometers are produced, as measurement of the film thickness of an SOI layer of an SOI wafer, each point measurement of film thickness by spectroscopic ellipsometry, reflection spectroscopy, or the like is generally performed, but, due to the influence of the wavelength of light used for measurement, spatial resolution has limitations to measure up to about hundreds of nanometers.

To evaluate the influence of the film thickness of an SOI layer on the SOI device characteristics adequately, it is necessary to measure the film thickness of an SOI layer with a spatial resolution of a few nanometers which is smaller than or equal to the channel size of a transistor.

Now, as an existing method for measuring the film thickness of a thin film, in Patent Document 1, for example, measuring the film thickness by irradiating a two-layer film with X-rays and measuring the characteristic X-rays generated from each film is described.

Patent Document 2 describes that, as a method for measuring the thickness of a thin film in a structure with a substrate on which a thin film is formed, a method of measurement using fluorescent X-rays is known. Furthermore, Patent Document 2 describes that the intensity of first fluorescent X-rays generated from the thin film and the intensity of second fluorescent X-rays generated from the substrate and attenuated as a result of passing through the thin film are measured at the same time.

Patent Document 3 describes that, as an explanation of a fluorescent X-ray film thickness analyzer, a thin film on a base substrate (a standard sample substrate) is irradiated with primary X-rays and the fluorescent X-rays generated from the thin film and the base substrate are detected, whereby it is possible to find out the composition and the film thickness of the thin film.

Patent Document 1: Japanese Unexamined Patent Publication (Kokai) No. H05-45147
Patent Document 2: Japanese Unexamined Patent Publication (Kokai) No. 2002-213935
Patent Document 3: Japanese Unexamined Patent Publication (Kokai) No. H10-221047

SUMMARY OF INVENTION

Technical Problem

However, since the thin film is irradiated with X-rays in the existing techniques described in Patent Documents 1, 2, and 3, it is difficult to perform accurate measurement of film thickness because both effects of attenuation of the emitted X-rays themselves and attenuation of the generated fluorescent X-rays overlap. Moreover, in cases where, for example, the film thickness of a thin film is extremely small as in an SOI layer of an SOI wafer used for fabrication of an FD-SOI device, the fluorescent X-rays generated from a base are not adequately attenuated even after passing through the thin film, making it impossible to perform accurate conversion into a film thickness. Furthermore, in the present X-ray optical system, the irradiation diameter of X-rays can be reduced only to about 10 μm, which makes it impossible to obtain a spatial resolution of a target microscopic area ranging from a few nanometers to hundreds of nanometers.

In addition, in spectroscopic ellipsometry or reflection spectroscopy which is a common method for measuring the film thickness of an SOI layer, as described above, spatial resolution has undesirably limitations to measure up to about hundreds of nanometers which is the wavelength of light.

The present invention was accomplished in view of the aforementioned circumstances, and its object is to provide a method for measuring the film thickness of an SOI layer of an SOI wafer, the method that can measure the film thickness of an SOI layer of an SOI wafer accurately with high spatial resolution in a microscopic area in the SOI layer even when the film thickness of the SOI layer of the SOI wafer is small.

Solution to Problem

To attain the above-described object, the present invention provides a method for measuring a film thickness of an SOI layer of an SOI wafer including at least an insulator layer and the SOI layer which is formed on the insulator layer and is formed of a silicon single crystal, wherein a surface of the SOI layer is irradiated with an electron beam, characteristic X-rays are detected from a side of the SOI layer surface irradiated with the electron beam, characteristic X-rays being generated by exciting a specific element in the insulator layer with the electron beam that has passed through the SOI layer and has been attenuated in the SOI layer, and the film thickness of the SOI layer is calculated on the basis of an intensity of the detected characteristic X-rays.

With such a method, since measurement is performed by irradiating the surface of an SOI layer with an electron beam, the emitted electron beam can be attenuated reliably when the electron beam is made to pass through the SOI layer. Furthermore, since characteristic X-rays generated as a result of a specific element in the insulator layer being excited are hardly attenuated in a thin SOI layer, it is possible to measure the film thickness of the SOI layer accurately by using the characteristic X-rays.

Moreover, since the electron beam has a short wavelength, is less affected by refraction, and has high light harvesting, it is possible to irradiate an extremely microscopic area with the electron beam and thereby measure the film thickness of the SOI layer with high spatial resolution.

In addition, since the film thickness of the SOI layer is measured by generating characteristic X-rays by exciting, by the electron beam, a specific element in the insulator layer formed immediately below the SOI layer, it is possible to measure with ease and efficiency.

Moreover, at this time, the insulator layer is a silicon oxide film, and the SOI wafer is made up of a base wafer formed of a silicon single crystal, the silicon oxide film formed on the base wafer, and the SOI layer formed on the silicon oxide film.

In measurement of the film thickness of an SOI layer of such an SOI wafer with a common structure, the present invention is especially effective.

Furthermore, at this time, it is preferable that the specific element is an oxygen atom in the silicon oxide film.

In the method, since a large amount of oxygen atom is contained in the silicon oxide film, there is no need to prepare another specific element, making it possible to measure the film thickness of the SOI layer more efficiently.

Moreover, at this time, the film thickness of the SOI layer may be set at 200 nm or less.

As described above, in the present invention, even with a thin SOI layer with a film thickness of 200 nm or less, by irradiating the surface thereof with an electron beam, the electron beam is attenuated adequately when the electron beam passes through the SOI layer, making it possible to measure the film thickness of the SOI layer accurately.

Furthermore, at this time, a beam diameter of the electron beam with which the surface of the SOI layer is irradiated may be set at 400 nm or less.

In the method, it is possible to set an area in which the film thickness of an SOI layer is to be measured at a microscopic area with a diameter of 400 nm or less and thereby measure the film thickness of an SOI layer accurately with higher spatial resolution.

Moreover, at this time, the film thickness of the SOI layer is measured by a scanning electron microscope, and the electron beam to be emitted is an electron beam of the scanning electron microscope.

As described above, the method of measurement of the present invention can be performed by using the scanning electron microscope and there is no need to build another device, making it possible to measure the film thickness of the SOI layer efficiently at lower cost.

Advantageous Effects of Invention

As described above, according to the present invention, since measurement is performed by irradiating the surface of an SOI layer with an electron beam, it is possible to measure the film thickness of the SOI layer accurately and irradiate an extremely microscopic area with the electron beam, which makes it possible to measure the film thickness of the SOI layer with high spatial resolution. As a result, it is possible to evaluate the influence of a film thickness of an SOI layer on device characteristics adequately.

BRIEF DESCRIPTION OF DRAWINGS

FIG. 1 is a diagram showing the relationship between the characteristic X-ray intensity ratio I and the film thickness D of an SOI layer in Example.

DESCRIPTION OF EMBODIMENTS

The inventor researched in a method for accurate measuring the film thickness of an extremely thin SOI layer, such as an SOI layer of an SOI wafer used for fabrication of an FD-SOI device, with high spatial resolution. And the inventor of the present invention has thought that, if an SOI layer of an SOI wafer is irradiated with an electron beam, since the electron beam is adequately attenuated according to the film thickness of the SOI layer when passing through the SOI layer and reaches a base, conversion into the film thickness of the SOI layer can be performed by measuring the intensity of characteristic X-rays (fluorescent X-rays) generated from the base.

That is, while the electron beam is adequately attenuated in proportion to the film thickness of the SOI layer when passing through the SOI layer even when the SOI layer is extremely thin, attenuation of the characteristic X-rays generated from the base when the characteristic X-rays pass through the SOI layer is incomparably small. In addition to this, with the electron beam, it is possible to reduce the beam diameter to about a few nanometers. Therefore, the inventor of the present invention has thought that, by using these properties, it is possible to measure the film thickness of an extremely thin SOI layer accurately with high spatial resolution and completed the present invention.

Hereinafter, as an example of an embodiment of the present invention; a method for measuring the film thickness of an SOI layer of an SOI wafer, the method using a scanning electron microscope (SEM: Scanning Electron Microscope), will be described in detail. However the present invention is not limited thereto.

Here, the SEM is first described briefly. The SEM obtains information of an object by irradiating part of the object with an electron beam emitted from a probe and thereby detecting a secondary electron, a reflection electron, a transmission electron, X-rays, cathode luminescence (fluorescence), an internal electromotive force, and so forth emitted from the object, constructs an image of the object based on each information thus obtained by making the electron beam scan the whole of the object, and displays the image.

The commonly-used SEM has the function of analyzing the component elements of a microscopic object to be observed by energy dispersive X-ray spectrometry (EDX: Energy Dispersive X-ray Spectrometry) (a scanning electron microscope with this function is sometimes called a SEM-EDX).

EDX is a method for performing elemental analysis or composition analysis by detecting characteristic X-rays that are generated by irradiation with an electron beam and dispersing the characteristic X-rays depending on energy.

By using this SEM-EDX, several kinds of SOI wafers having SOI layers with known their film thicknesses are first prepared, the surfaces of these SOI layers are irradiated with an electron beam by a probe, and the intensity of characteristic X-rays emitted as a result of the electron beam passing through each SOI layer, reaching an insulator film (for example, a silicon oxide film or the like), and exciting a specific element (for example, oxygen or the like) in the insulator film is measured from the surface side irradiated with the electron beam. In this way, the characteristic X-ray intensities of the SOI wafers having the SOI layers with diverse film thicknesses are measured, and the relationship between the film thickness of the SOI layer and the characteristic X-ray intensity is obtained in advance.

Here, for example, the characteristic X-ray intensity Io from an oxygen atom has a relation indicated in the expression (1) with the film thickness D (nm) of the SOI layer and the electron beam penetration length L (nm). The value of L is obtained from the acceleration voltage of the electron beam set at this time, the values of D are calculated from the measured values of Io, and an approximate line of Io and D is obtained from these data.

$$Io = A \cdot \exp(-D/L) \text{ (where } A \text{ is a constant)} \quad \text{Expression (1):}$$

In so doing, assuming that the intensity of an electron beam to be emitted slightly varies between each measurement, for the purpose of correcting the variation, in addition to the characteristic X-ray intensity of a specific element, the characteristic X-ray intensity from another specific element (for example, silicon or the like) near a position in which measurement is to be performed and in a portion with an SOI layer film thickness of a predetermined constant value is also measured as a reference, and the characteristic X-ray intensity ratio is determined from these two characteristic X-ray intensities, which makes it also possible to obtain the relationship between the characteristic X-ray intensity ratio and the film thickness of the SOI layer. When the intensity of the electron beam is extremely stable, the relationship between the characteristic X-ray intensity of a specific element and the film thickness of the SOI layer can be obtained directly.

When the characteristic X-ray intensity ratio is used, in expression (1) above, the characteristic X-ray intensity Io is equal to the characteristic X-ray intensity ratio I (Io=I).

Incidentally, in addition to preparing several kinds of SOI wafers with known film thicknesses and performing measurement as described above, the relationship between the film thickness of the SOI layer and the characteristic X-ray intensity (ratio) may be obtained by preparing one SOI wafer with a known film thickness, the SOI wafer having a defect or the like (a defect with fluctuations of the film thickness) caused by fluctuations of the SOI layer film thickness, the SOI wafer with an SOI layer whose film thickness varies greatly, and determining the characteristic X-ray intensities (ratios) in positions in which measurement is to be performed, the positions with different known film thicknesses, on the surface of the SOI layer of the SOI wafer.

Then, in the manner similar to the above-described measurement procedure, the characteristic X-ray intensity of a specific element, the characteristic X-ray intensity obtained by irradiating, with an electron beam, an SOI layer to be measured of an SOI wafer with an SOI layer whose film thickness is unknown is measured, and the unknown film thickness of the SOI layer is calculated on the basis of the above-described relationship obtained in advance. In so doing, the film thickness of the SOI layer may be calculated by determining the characteristic X-ray intensity ratio in the manner similar to the above-described method.

At this time, as an SOI layer to be measured of an SOI wafer, the present invention is especially effective for a thin SOI layer with a film thickness of 200 nm or less.

Since, unlike photons, electrons forming the electron beam used in the method of measurement of the present invention have electric charges, the interaction of the electrons with other substances is strong.

As a result, it is possible to measure accurately the film thickness of such an SOI layer with a small film thickness because the electron beam is reliably attenuated when passing through the SOI layer, reaches a specific element of an insulator layer, and generates characteristic X-rays having an intensity according to the intensity of the electron beam that has reached the specific element of the insulator layer.

Moreover, since an electron beam having high light condensing property is used in the method of measurement of the present invention, it is possible to set the beam diameter of the electron beam with which the surface of an SOI layer is irradiated at 400 nm or less, preferably at 100 nm or less, and more preferably at 50 nm or less. This makes it possible to achieve an extremely microscopic SOI layer film thickness measurement area and measure the film thickness of the SOI layer with high spatial resolution. A lower limit of the beam diameter is not limited to a particular value; it is quite possible to reduce the lower limit actually to about 1 nm and, theoretically, it is also possible to reduce the lower limit to 0.1 nm or less.

In general, an SOI wafer made up of a base wafer formed of a silicon single crystal, a silicon oxide film formed on the base wafer, and an SOI layer formed of a silicon single crystal, the SOI layer formed on the silicon oxide film, has been widely used. Therefore, adopting an oxygen atom in the silicon oxide film as the specific element described above is more efficient.

Moreover, for example, when measurement is performed by using an SOI wafer having, as an insulator layer, an oxide film obtained by thermally oxidizing a silicon single crystal wafer containing a high concentration of boron or measurement is performed by using an SOI wafer using a silicon nitride film as an insulator layer, boron or nitrogen in the insulator layer can also be used as a specific element.

Here, it is assumed that the accelerating energy of an electron beam to be emitted is greater than the binding energy of a K core electron of each specific element. For example, when the specific element is oxygen, boron, or nitrogen, the accelerating energy of an electron beam to be emitted is 532 eV or more, 188 eV or more, or 399 eV or more respectively.

The smaller the accelerating energy, the shorter the electron beam penetration length and therefore the higher the film thickness measurement sensitivity. Thus, to raise the precision of measurement of film thickness, it is preferable to set the accelerating energy of an electron beam to be emitted at the lowest possible value which is greater than the binding energy of the K shell electron, but, if the accelerating energy is too low, the electron beam may not reach the insulator layer to a satisfactory extent. Therefore, it is necessary to set the accelerating energy as appropriate with consideration given to the film thickness of an SOI layer to be measured.

In the method of measurement of the present invention, before an SOI layer is irradiated with an electron beam, it is preferable to remove a native oxide film on the surface of the SOI layer, the native oxide film which causes an error of measurement. Moreover, even when the native oxide film is not removed, it is also possible to eliminate the error caused by the surface native oxide film by measuring the characteristic X-rays of a specific element (oxygen) from the surface native oxide film by using a mirror-polished wafer subjected to the same treatment (such as RCA cleaning) as that performed on an SOI wafer to be measured and subtracting the value of the characteristic X-ray intensity from the value of the measurement result.

Moreover, since the present invention is a method for detecting the characteristic X-rays generated from a base after making an electron beam pass through an SOI layer to be measured, the spatial resolution of SOI layer film thickness measurement is determined by the beam diameter observed when an electron beam emitted after the diameter of the beam was reduced passes through a thin SOI layer. Therefore, even when the beam that has entered the base after passing through the SOI layer excites characteristic X-rays in a state in which the beam diameter spreads in the base, since the spread does not affect the spatial resolution of SOI layer film thickness measurement, it is possible to maintain high spatial resolution.

EXAMPLE

Hereinafter, the present invention will be described more specifically with an example and comparative examples, but the present invention is not limited to these examples.

Example

First, an SOI wafer produced by the ion implantation delamination method and made up of a base wafer formed of a silicon single crystal, a silicon oxide film formed on the base wafer, and an SOI layer formed on the silicon oxide film, the SOI wafer having a defect caused by fluctuations of the SOI layer film thickness, was prepared.

Then, four spots (positions in which measurement is to be performed) on the surface of the SOI layer, the spots whose film thicknesses measured by spectroscopic ellipsometry were 30, 70, 120, and 200 nm, were irradiated with an electron beam (a beam diameter 30 nm, an acceleration voltage 5 kV) by using a SEM-EDX (SEM Vision G3 manufactured by Applied Materials, Inc.), and the characteristic X-ray intensity Io generated as a result of the electron beam having passed through the SOI layer, reached the silicon oxide film, and excited an oxygen atom in the silicon oxide film was measured from the side of the SOI layer surface irradiated with the electron beam. Incidentally, the native oxide film on the SOI layer surface before being irradiated with the electron beam was removed by hydrofluorination.

In so doing, the characteristic X-ray intensity Is from a silicon atom near each position in which measurement was to be performed and in a portion with an SOI layer film thickness of 70 nm was also measured as a reference, and the characteristic X-ray intensity ratio I (=Io/Is) was determined.

When the acceleration voltage of the electron beam was set at 5 kV, since the electron beam penetration length L was about 130 nm, 1/L was 0.0077. This value was substituted into the expression (1) above, and the measurement result of the characteristic X-ray intensity ratio was substituted into the expression thus obtained to obtain the film thickness of the SOI layer. When an approximate line was obtained from these measurement result and calculation result, expression (2) was obtained. The results thus obtained are listed in Table 1 below and depicted in FIG. 1.

$$I=0.66\exp(-0.0077D) \quad \text{Expression (2):}$$

Next, an SOI wafer produced by the ion implantation delamination method and made up of a base wafer formed of a silicon single crystal, a silicon oxide film formed on the base wafer, and an SOI layer formed on the silicon oxide film, the SOI layer whose film thickness was unknown, was prepared. And the SOI wafer had a defect caused by fluctuations of the film thickness.

Then, three positions on the SOI layer surface in which measurement was to be performed and a defect with fluctuations of the film thickness was present were set at intervals of 10 μm, the positions were irradiated with an electron beam by using a SEM-EDX, and the characteristic X-ray intensity Io generated as a result of the electron beam having passed through the SOI layer, reached the silicon oxide film, and excited an oxygen atom in the silicon oxide film was measured from the side of the SOI layer surface irradiated with the electron beam. The native oxide film on the SOI layer surface before being irradiated with the electron beam was removed by hydrofluorination.

In so doing, the characteristic X-ray intensity Is from a silicon atom near each position in which measurement was to be performed and in a portion with an SOI layer film thickness of 70 nm was also measured as a reference, and the characteristic X-ray intensity ratio I (=Io/Is) was determined. Then, this value was substituted into the expression (2) above to obtain the film thickness D of the SOI layer. The results are listed in Table 2 below.

As is clear from the results listed in Table 2, according to the present invention, since an electron beam is used, even when the film thickness of an SOI layer is small, it is possible to measure accurately the film thickness of an extremely microscopic area of the SOI layer and evaluate film thickness variations with precision. Moreover, by increasing the number of measurement points, it is also possible to create a film thickness map of the SOI layer.

Comparative Example 1

Measurement of the film thickness of an SOI layer was performed on an area including three points measured in Example, the three points of an SOI wafer having a defect with fluctuations of the film thickness, by using a film thickness measuring device (ASET-F5x manufactured by KLA-Tencor) using spectroscopic ellipsometry. As a result, the result was that the film thickness measured was 70 nm.

However, since the measuring beam with a diameter of about 30 μm was used in this measurement, the measurement value merely indicated an average film thickness in an area with a diameter of about 30 μm, and it was impossible to measure the film thickness of a more microscopic area.

Comparative Example 2

Measurement of the film thickness of an SOI layer was performed on an area including three points measured in Example, the three points of an SOI wafer having a defect with fluctuations of the film thickness in the same manner as in Example except that a fluorescent X-ray film thickness analyzer described in Patent Document 3 was used. As a result, the emitted X-rays were hardly attenuated in the SOI layer, making it impossible to obtain an accurate measurement result.

Moreover, even when the measurement result could be obtained, since this measurement used X-rays with a beam diameter of about 10 μm, the measured value merely indicated an average film thickness in an area with a diameter of about 10 μm, and it is predicted that measurement of the film thickness of a more microscopic area could not be performed.

TABLE 1

| | SOI film thickness: D (nm) | | | |
| --- | --- | --- | --- | --- |
| | 30 | 70 | 120 | 200 |
| Characteristic X-ray intensity of O: Io (a.u.) | 5.1 | 3.8 | 2.3 | 1.2 |
| Characteristic X-ray intensity of Si: Is (a.u.) Ref. | 9.6 | 9.6 | 9.3 | 8 |
| Characteristic X-ray intensity ratio: I (=Io/Is) | 0.531 | 0.396 | 0.247 | 0.150 |

TABLE 2

| | Measurement 1 | Measurement 2 | Measurement 3 |
| --- | --- | --- | --- |
| Characteristic X-ray intensity of O: Io (a.u.) | 4.2 | 3.8 | 3.4 |
| Characteristic X-ray intensity of Si: Is (a.u.) Ref. | 9.6 | 9.5 | 9.7 |
| Characteristic X-ray intensity ratio: I (=Io/Is) | 0.438 | 0.400 | 0.351 |
| SOI film thickness (nm) | 53 | 65 | 82 |

Incidentally, in Example, in addition to the characteristic X-ray intensity of an oxygen atom, the characteristic X-ray intensity from a silicon atom was also measured as a reference, and the characteristic X-ray intensity ratio was determined from these two characteristic X-ray intensities. However, when the intensity of an electron beam is extremely stable, the relationship between the characteristic X-ray intensity of an oxygen atom and the film thickness of an SOI layer may be directly obtained.

Moreover, in addition to the method for performing measurement by preparing an SOI wafer having a defect or the like caused by fluctuations of the film thickness of the SOI layer, measurement may be performed by preparing several kinds of SOI wafers with known film thicknesses. Furthermore, when a large amount of boron, nitrogen, or the like is contained in an insulator layer, these elements may be used as a specific element.

The present invention is not limited to the embodiment described above. The above-described aspects are mere examples and those having substantially the same structure as technical ideas described in the appended claims and providing the similar functions and advantages are included in the scope of the present invention.

The invention claimed is:

1. A method for measuring a film thickness of an SOI layer of an SOI wafer including at least an insulator layer and the SOI layer which is formed on the insulator layer and is formed of a silicon single crystal, comprising
    removing a native oxide film on the surface of the SOI layer or eliminating an error caused by the native oxide film by measuring characteristic X-rays of a specific element from a surface native oxide film of a mirror-polished wafer subjected to a same treatment as that performed on the SOI wafer, then
    irradiating a surface of the SOI layer with an electron beam, detecting characteristic X-rays from a side of the SOI layer surface irradiated with the electron beam, the characteristic X-rays being generated by exciting the specific element in the insulator layer with the electron beam that has passed through the SOI layer and has been attenuated in the SOI layer, and calculating the film thickness of the SOI layer on the basis of an intensity of the detected characteristic X-rays,
    wherein the insulator layer is a silicon oxide film, the SOI wafer is made up of a base wafer formed of a silicon single crystal, the silicon oxide film formed on the base wafer, and the SOI layer formed on the silicon oxide film, and the specific element is an oxygen atom in the silicon oxide film.

2. The method for measuring a film thickness of an SOI layer of an SOI wafer according to claim 1, wherein
    the film thickness of the SOI layer is set at 200 nm or less.

3. The method for measuring a film thickness of an SOI layer of an SOI wafer according to claim 2, wherein
    a beam diameter of the electron beam with which the surface of the SOI layer is irradiated is set at 400 nm or less.

4. The method for measuring a film thickness of an SOI layer of an SOI wafer according to claim 1, wherein
    a beam diameter of the electron beam with which the surface of the SOI layer is irradiated is set at 400 nm or less.

5. The method for measuring a film thickness of an SOI layer of an SOI wafer according to claim 1, wherein,
    the film thickness of the SOI layer is measured by a scanning electron microscope, and the electron beam to be emitted is an electron beam of the scanning electron microscope.

* * * * *